(12) United States Patent
Cordaro et al.

(10) Patent No.: US 9,872,716 B2
(45) Date of Patent: Jan. 23, 2018

(54) ARTICULATING ROD BENDER AND CUTTER

(71) Applicant: INNOVASIS DEVELOPMENT PARTNERS, LLC, Salt Lake City, UT (US)

(72) Inventors: Nicholas Michael Cordaro, Vista, CA (US); David Gabriel Malmberg, Encinitas, CA (US)

(73) Assignee: Innovasis Development Partners, LLC, Salt Lake City, UT (US)

( * ) Notice: Subject to any disclaimer, the term of this patent is extended or adjusted under 35 U.S.C. 154(b) by 0 days.

(21) Appl. No.: 14/869,307

(22) Filed: Sep. 29, 2015

(65) Prior Publication Data

US 2016/0089195 A1  Mar. 31, 2016

Related U.S. Application Data

(60) Provisional application No. 62/056,829, filed on Sep. 29, 2014.

(51) Int. Cl.
*A61B 17/88* (2006.01)
*A61B 17/70* (2006.01)
(Continued)

(52) U.S. Cl.
CPC ...... *A61B 17/8863* (2013.01); *A61B 17/7002* (2013.01); *A61B 17/7085* (2013.01);
(Continued)

(58) Field of Classification Search
CPC ......... A61B 17/8863; B21D 7/08; B21D 9/10
See application file for complete search history.

(56) References Cited

U.S. PATENT DOCUMENTS 1,047,612 A * 12/1912 Frederick ............... B21D 7/08
                                                                               72/173
2,335,028 A * 11/1943 Rose ..................... B21D 7/08
                                                                               72/171
(Continued)

FOREIGN PATENT DOCUMENTS

EP        2 705 803 A2     3/2014

OTHER PUBLICATIONS

International Search Report dated Jan. 29, 2016, issued in PCT Application No. PCT/US2015/052925, filed Sep. 29, 2015.

*Primary Examiner* — Julianna N Harvey
(74) *Attorney, Agent, or Firm* — Workman Nydegger

(57) ABSTRACT

An articulating surgical rod bender assembly includes first and second support members pivotably connected at an interface, a first drive wheel rotatably attached to the first support member, a second drive wheel rotatably attached to the first support member and coupled with the first drive wheel, and means for rotating the first drive wheel so that rotation of the first drive wheel causes rotation of the second drive wheel to advance a surgical rod through the assembly. The assembly also includes a guide element selectively positionable so that a surgical rod positioned with a first side contacting the first drive wheel, an opposing second side contacting the second drive wheel, and one of the first and second sides contacting the guide element is bent to a desired curvature or radius of curvature by the guide element and the first and/or second drive wheels as is passes through the assembly.

13 Claims, 13 Drawing Sheets

(51) Int. Cl.
*B23D 29/02* (2006.01)
*B21D 7/08* (2006.01)

(52) U.S. Cl.
CPC ........ *B23D 29/023* (2013.01); *A61B 17/7013* (2013.01); *B21D 7/08* (2013.01)

(56) References Cited

U.S. PATENT DOCUMENTS

2011/0107601 A1 5/2011 Crainich et al.
2012/0247173 A1 10/2012 Paris et al.

* cited by examiner

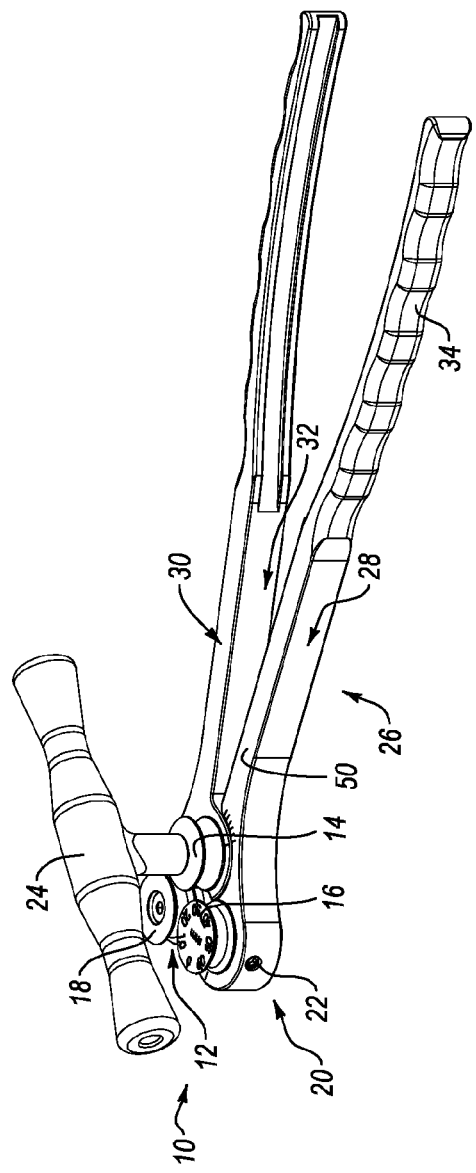
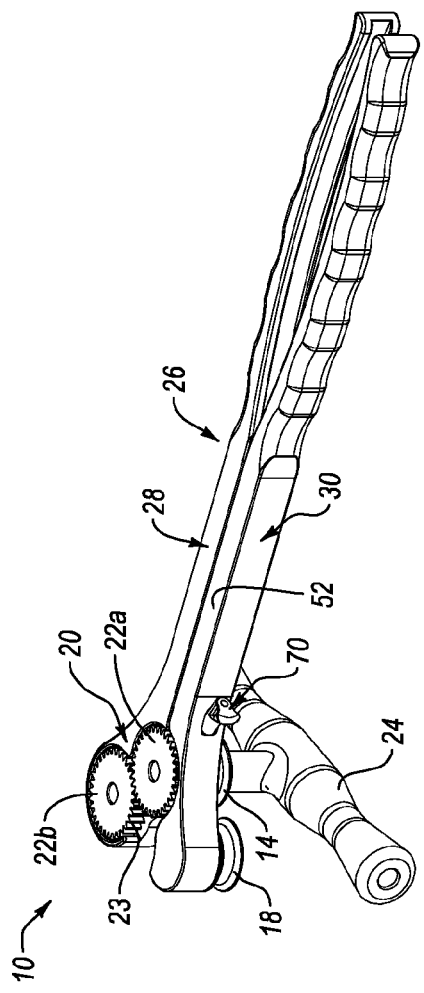

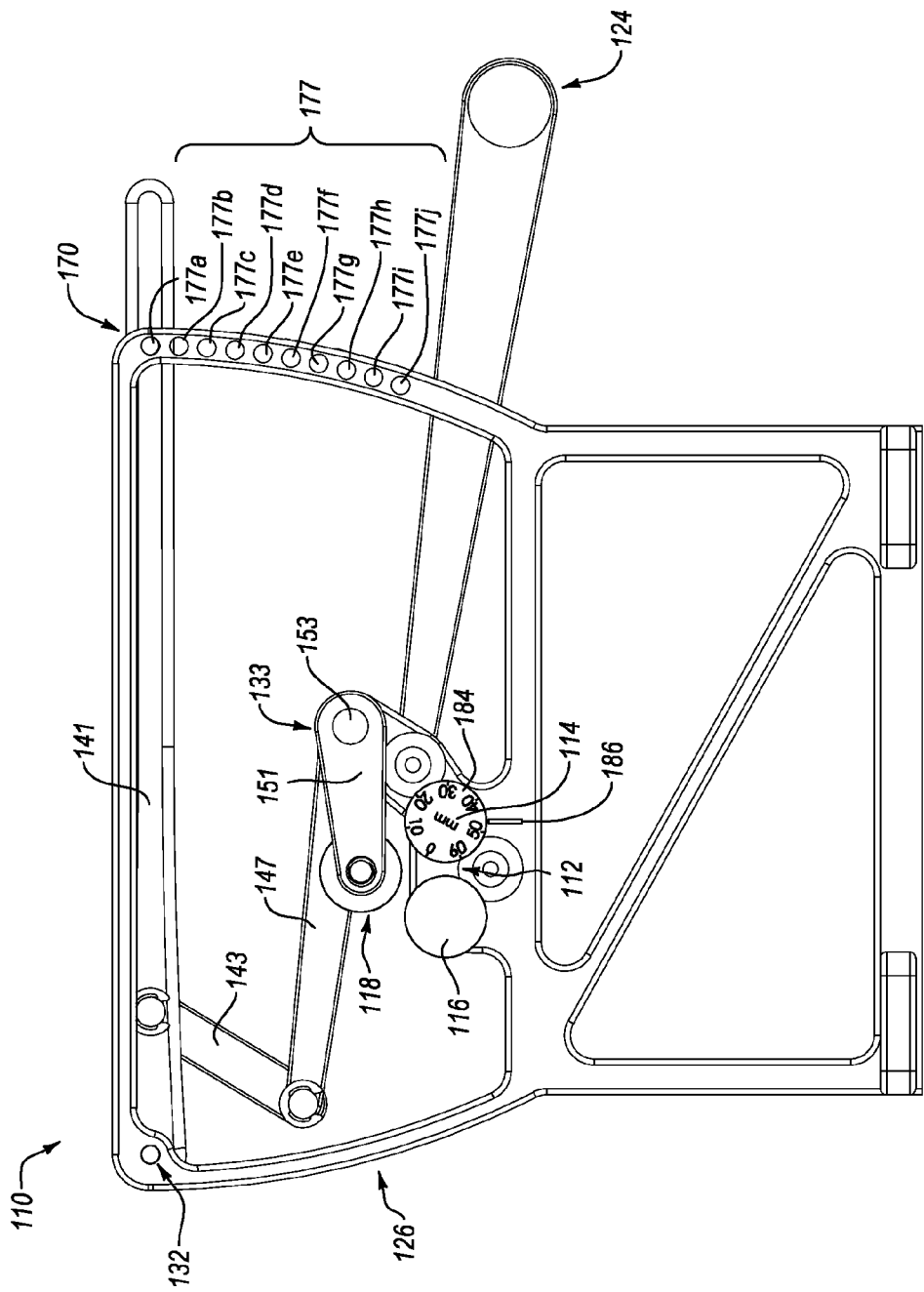

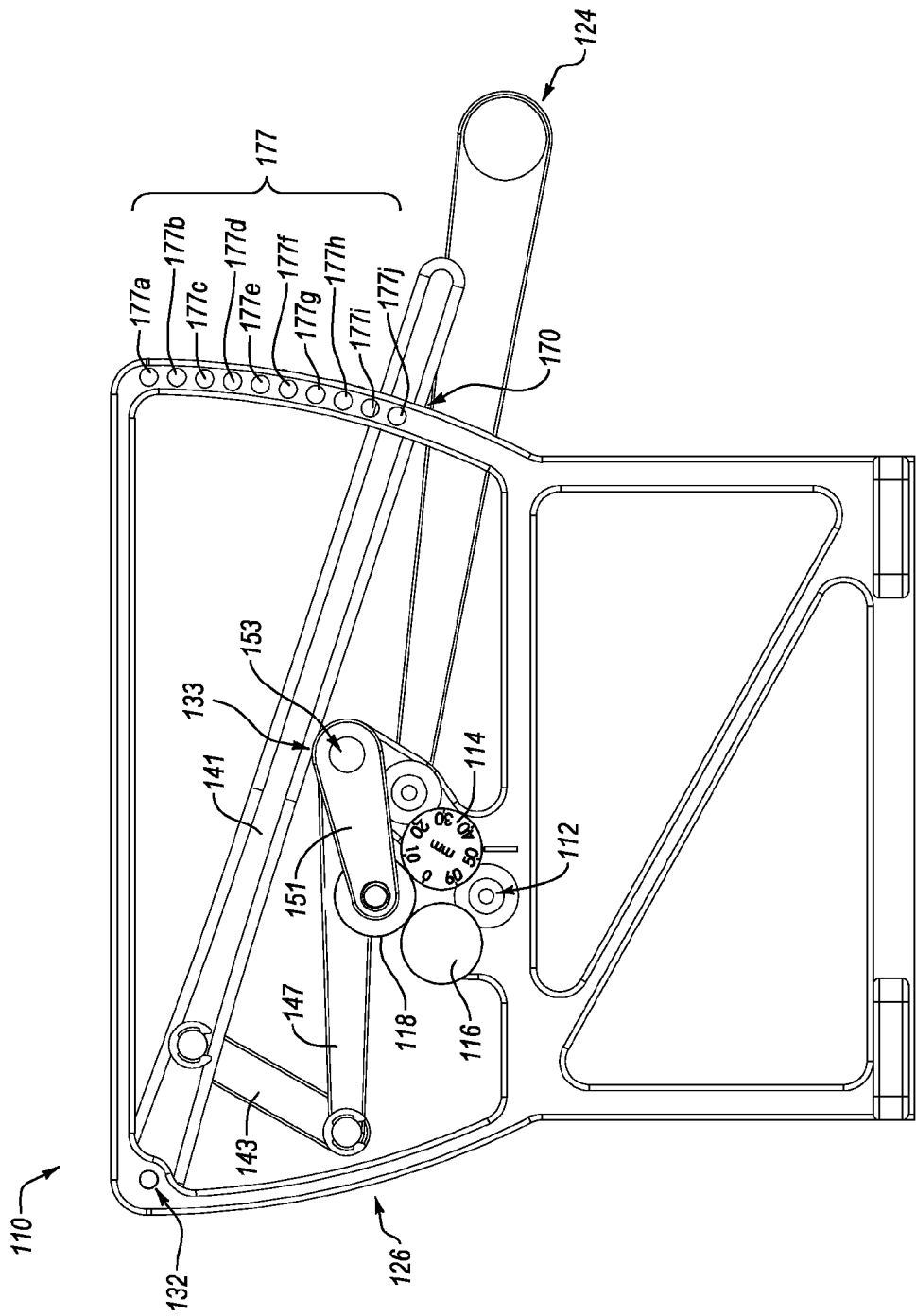

ARTICULATING ROD BENDER AND CUTTER

CROSS-REFERENCE TO RELATED APPLICATIONS

This application is claims the benefit of U.S. Provisional Application Ser. No. 62/056,829, filed Sep. 29, 2014, which application is incorporated herein by specific reference.

BACKGROUND OF THE INVENTION

1. The Field of the Invention

The present disclosure relates to surgical equipment, and more particularly to devices and systems for bending implantable surgical rods, and methods of performing the same.

2. The Relevant Technology

A variety of surgical procedures involve implanting a rigid support structure in the body of the patient. For instance, spinal surgical methods often include forming a spinal implant that matches the contours of the patient's spine and then installing the implant onto the spinal column. The rigid support structure of the spinal implant can be formed of elongated surgical rods that are pre-bent or custom bent for the patient. Existing devices and methods for on demand, custom surgical rod bending require a high amount of force applied to one or more bending locations along the length of the surgical rod. This force often includes physical exertion applied to an apparatus designed to bend the rod around a bending point. However, some users may not have the physical strength necessary to apply the force required to bend the rod.

Moreover, existing rod bending solutions produce a non-uniform and/or segmented bend in the surgical rod. For instance, to produce a rod having a desired curvature or radius of curvature, the linear rod may be bent to a first curvature or radius of curvature at a plurality of distinct locations along the length of the rod. This is accomplished with existing devices by disposing a first portion of the rod in the device, clamping down on the first portion of the rod to produce the desired curvature or radius of curvature at a first location, unclamping or opening the device, moving the rod so that a second portion is disposed in the device, clamping down on the second portion of the rod to produce the desired curvature or radius of curvature at a second location, and so forth. Accordingly, the rod is bent to the desired curvature or radius of curvature along the length of the rod by forming multiple bent segments rather than by producing a smooth and/or uniform curve the bent rod comprising a plurality of bent segments, rather than a smooth, uniform curve.

Accordingly, there are a number of disadvantages to existing surgical rod bending devices and methods that can be addressed.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 1A is a top perspective view of an articulating surgical rod bender assembly according to an embodiment of the present disclosure;

FIG. 1B is a bottom perspective view thereof;

FIG. 8A is a front elevation view thereof in an open configuration;

FIG. 8B is a front elevation view thereof in an open configuration;

DETAILED DESCRIPTION OF THE PREFERRED EMBODIMENTS

Figure 2:
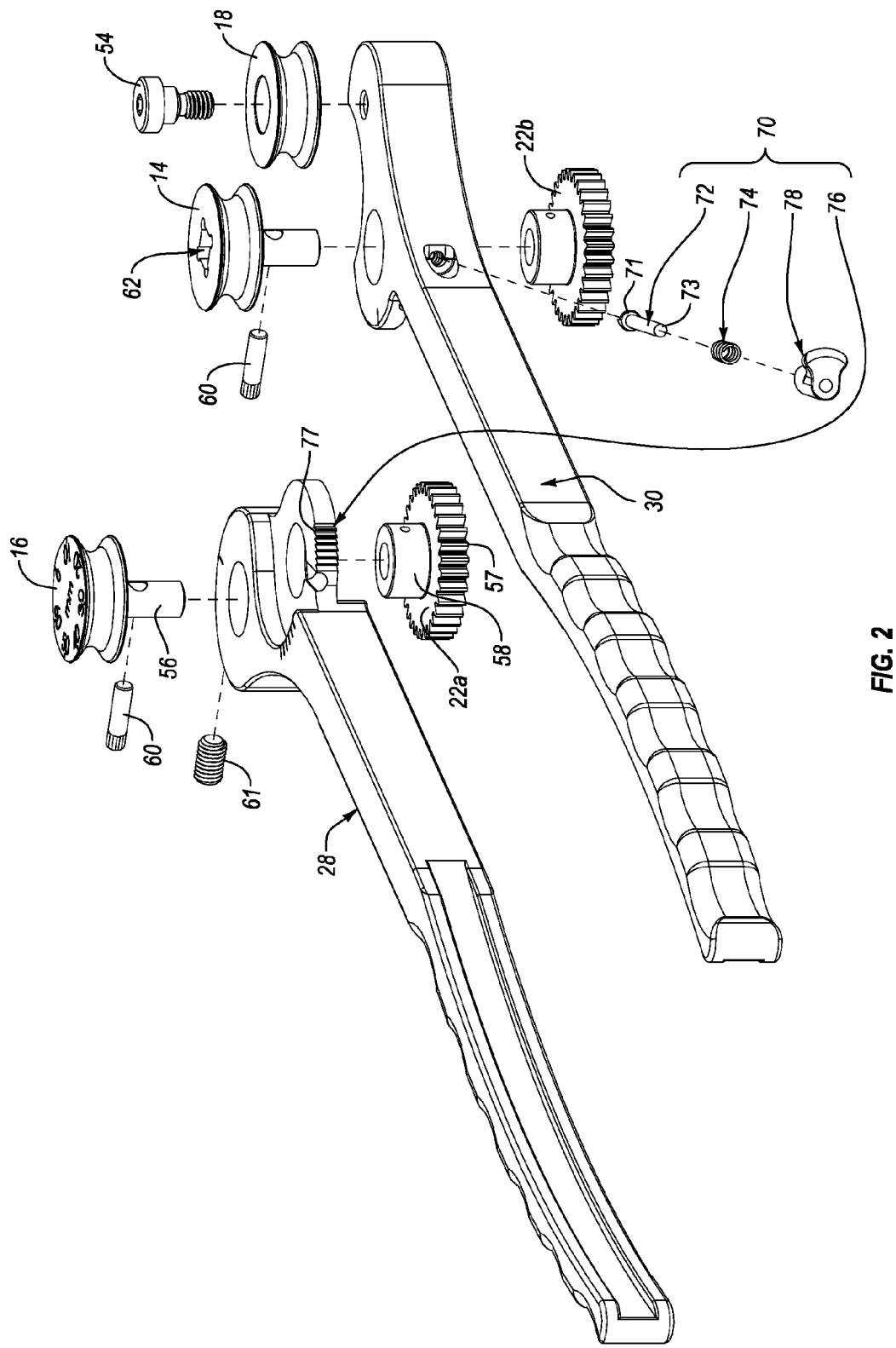
FIG. 2 is an exploded view thereof.

Before describing the present disclosure in detail, it is to be understood that this disclosure is not limited to the specific parameters of the particularly exemplified systems, apparatus, assemblies, products, devices, kits, methods, and/or processes, which may, of course, vary. It is also to be understood that much, if not all of the terminology used herein is only for the purpose of describing particular embodiments of the present disclosure, and is not necessarily intended to limit the scope of the disclosure in any particular manner. Thus, while the present disclosure will be described in detail with reference to specific configurations, embodiments, and/or implementations thereof, the descriptions are illustrative only and are not to be construed as limiting the scope of the claimed invention.

Various aspects of the present disclosure, including devices, systems, methods, etc., may be illustrated with reference to one or more embodiments or implementations, which are exemplary. As used herein, the terms "embodiment" and/or "implementation" mean "serving as an example, instance, or illustration," and should not necessarily be construed as preferred or advantageous over other embodiments or implementations disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the following description.

Furthermore, unless defined otherwise, all technical and scientific terms used herein have the same meaning as commonly understood by one of ordinary skill in the art to which the present disclosure pertains. While a number of methods, materials, components, etc. similar or equivalent to those described herein can be used in the practice of the present disclosure, only certain exemplary methods, materials, components, etc. are described herein.

It will be noted that, as used in this specification and the appended claims, the singular forms "a," "an" and "the" include plural referents unless the content clearly dictates otherwise. Thus, for example, reference to a "column" includes one, two, or more columns. Similarly, reference to a plurality of referents should be interpreted as comprising a single referent and/or a plurality of referents unless the content and/or context clearly dictate otherwise. Thus, reference to "columns" does not necessarily require a plurality of such columns. Instead, it will be appreciated that independent of conjugation; one or more columns are contemplated herein.

As used throughout this application the words "can" and "may" are used in a permissive sense (i.e., meaning having the potential to), rather than the mandatory sense (i.e., meaning must). Additionally, the terms "including," "having," "involving," "containing," "characterized by," as well as variants thereof (e.g., "includes," "has," and "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

Various aspects of the present disclosure can be illustrated by describing components that are coupled, attached, connected, and/or joined together. As used herein, the terms "coupled", "attached", "connected," and/or "joined" are used to indicate either a direct association between two components or, where appropriate, an indirect association with one another through intervening or intermediate components. In contrast, when a component is referred to as being "directly coupled", "directly attached", "directly connected," and/or "directly joined" to another component, no intervening elements are present or contemplated. Thus, as used herein, the terms "connection," "connected," and the like do not necessarily imply direct contact between the two or more elements. In addition, components that are coupled, attached, connected, and/or joined together are not necessarily (reversibly or permanently) secured or affixed to one another. For instance, coupling, attaching, connecting, and/or joining can comprise placing, positioning, and/or disposing the components together or otherwise adjacent in some embodiments.

As used herein, directional and/or arbitrary terms, such as "top," "bottom," "front," "back," "forward," "rear," "left," "right," "up," "down," "upper," "lower," "inner," "outer," "internal," "external," "interior," "exterior," "anterior," "posterior," "proximal," "distal," and the like can be used only for convenience and/or solely to indicate relative directions and/or orientations and may not otherwise be intended to limit the scope of the disclosure, including the specification, invention, and/or claims. According, such directional and/or arbitrary terms are not to be construed as necessarily requiring a specific order or position.

To facilitate understanding, like reference numerals have been used, where possible, to designate like elements common to the figures. Furthermore, alternative configurations of a particular element may each include separate letters appended to the element number. Accordingly, an appended letter can be used to designate an alternative design, structure, function, implementation, and/or embodiment of an element or feature without an appended letter. Similarly, multiple instances of an element and or sub-elements of a parent element may each include separate letters appended to the element number. In each case, the element label may be used without an appended letter to generally refer to instances of the element or any one of the alternative elements. Element labels including an appended letter can be used to refer to a specific instance of the element or to distinguish or draw attention to multiple uses of the element. However, element labels including an appended letter are not meant to be limited to the specific and/or particular embodiment(s) in which they are illustrated. In other words, reference to a specific feature in relation to one embodiment should not be construed as being limited to applications only within said embodiment.

It will also be appreciated that where two or more values, or a range of values (e.g., less than, greater than, at least, and/or up to a certain value, and/or between two recited values) is disclosed or recited, any specific value or range of values falling within the disclosed values or range of values is likewise disclosed and contemplated herein. Thus, disclosure of an illustrative measurement or distance less than or equal to about 10 units or between 0 and 10 units includes, illustratively, a specific disclosure of: (i) a measurement of 9 units, 5 units, 1 units, or any other value between 0 and 10 units, including 0 units and/or 10 units; and/or (ii) a measurement between 9 units and 1 units, between 8 units and 2 units, between 6 units and 4 units, and/or any other range of values between 0 and 10 units.

Various modifications can be made to the illustrated embodiments without departing from the spirit and scope of the invention as defined by the claims. Thus, while various aspects and embodiments have been disclosed herein, other aspects and embodiments are contemplated. It is also noted that systems, methods, apparatus, devices, products, processes, assemblies, kits, etc., according to certain embodiments of the present invention may include, incorporate, or otherwise comprise properties, features, aspects, steps, components, assemblies, members, and/or elements described in other embodiments disclosed and/or described herein. Thus, reference to a specific feature, aspect, steps, component, assembly, member, element, etc. in relation to one embodiment should not be construed as being limited to applications only within said embodiment. In addition, reference to a specific benefit, advantage, problem, solution, method of use, etc. in relation to one embodiment should not be construed as being limited to applications only within said embodiment.

The headings used herein are for organizational purposes only and are not meant to be used to limit the scope of the description or the claims.

Embodiments of the present disclosure include systems, methods, and devices related to surgical equipment, and more particularly to devices and systems for bending implantable surgical rods, and methods of performing the same. Certain embodiments of the present disclosure relate to a rod bender assembly, and more particularly to an articulating surgical rod bender assembly. The assembly can include a first drive wheel, a second drive wheel adjacent to the first drive wheel, and means for rotating the second drive wheel via rotating the first drive wheel. As used herein, "wheel" and similar terms include rotatable members having a circumferential surface and an axis or rotation. It will be appreciated, however, that such wheels need not be entirely and/or uniformly circular (i.e., with a constant and/or uniform radius from the axis of rotation). Furthermore, such wheels need not have a uniform circumferential surface. Indeed, certain advantages may be obtained by altering the shape, size, and/or other conformational characteristic(s) of the radius, circumference, thickness, etc. For instance, the wheel(s) described here may have a pulley-wheel configuration (e.g., with a concave and/or recessed circumferential surface) and/or an at least partially oblong radial shape (e.g., similar to a simple cam-wheel)

In some embodiments, the means for rotating can comprise a mechanical apparatus and/or assembly that provides and/or achieves a mechanical advantage in rotating the second drive wheel via rotating the first drive wheel. For instance, the means for rotating can include a gear assembly having at least a first gear member connected to the first and second drive wheels. Such a connection may allow and/or provide for simultaneous rotation of the first and second drive wheels. For instance, in some embodiments, the first and second drive wheels can each be (directly and/or indirectly) connected to the first gear member such that rotation of the first gear member can simultaneously rotate the first and second drive wheels.

In some embodiments, the first gear member can be (axially) connected to the first drive wheel and (radially and/or circumferentially) connected to a second gear member that is (axially) connected to the second drive wheel such that rotation of the first gear member rotates the first drive wheel and the second gear member, causing rotation of the second drive wheel. Accordingly, rotating a drive wheel can comprise (i) directly rotating the drive wheel, (i) rotating a rotational member (e.g., a handle) connected to the drive wheel such that the drive wheel is rotated thereby, (iii) rotating a gear member connected to the drive wheel, either directly or indirectly (e.g., via a rotational member and/or other gear member), and/or (iv) rotating a separate wheel connected (e.g., via a means for rotating) to the drive wheel.

The means for rotating can also include a third, fourth, fifth, and/or any number of additional gear members. In at least one embodiment, a third gear member can be circumferentially connected to the first gear member, which is axially connected to the first drive wheel such that rotation of the third gear member causes rotation of the first gear member, and thereby, rotation of the first drive wheel. The first gear member can also be circumferentially connected to a fourth gear member, which is circumferentially connected to the second gear member, which is axially connected to the second drive wheel such that each of the foregoing is rotated upon rotation of the other(s). In one or more embodiments, one or more gear members can be sized so as to provide a mechanical advantage in rotating a first component via rotating a second component. Thus, the gear assembly and/or gear member(s) thereof can be "geared" to provide mechanical advantage.

The means for rotating can also or alternatively include one or more moving parts. In some embodiments, the means for rotating can include a crank, a cam, a lever, a pulley, a pump, a hydraulic, and/or any other moving part(s) suitable for use therewith.

The assembly can also include a guide element disposed adjacent to one or more of the first and second drive wheels (i.e., adjacent to the first drive wheel and/or second drive wheel). The guide element can comprise a guide wheel in some embodiments. However, the guide element can alternatively comprise a (non-rotatable) member having at least one rod-bending surface. For instance, the guide element can comprise a post, a pivot, a rod, a block, or any other suitable structural configuration. In some embodiments, the assembly (and/or the first drive wheel, second drive wheel, and/or guide element thereof) can be selectively positionable into a plurality of configurations and/or positions. For instance, the assembly can be selectively configurable between an open position and a plurality of clamping positions.

In an exemplary open configuration and/or non-clamping position, the guide element may be separated from the first and/or second drive wheel such that a linear surgical rod may pass through the assembly without being substantially bent along a length thereof. In a first clamping position, however, the guide element may be disposed and/or positioned closer to the first and/or second drive wheel than in the open configuration such that the surgical rod can be bent by the assembly. For instance, in some embodiments, closing the rod bending assembly from the open configuration into the first clamping position can cause the guide element and one or more of the first drive wheel and second drive wheel to bend the portion of the surgical rod (disposed therebetween) to a first curvature or radius of curvature.

In one or more (e.g., each) clamping positions, the first drive wheel, second drive wheel, and guide element can be positioned so that a surgical rod can be positioned and/or disposed with a first side of the surgical rod contacting the first drive wheel, an opposing second side of the surgical rod contacting the second drive wheel, and one of the first side of the surgical rod and the second side of the surgical rod contacting the guide element. In such a configuration, a portion of the rod can be bent to the desired curvature or radius of curvature as the portion passes between the first drive wheel and the second drive wheel and between the guide wheel and one of the first drive wheel and the second drive wheel. Thus, the assembly can be configured such that the surgical rod can be advanced (longitudinally) therethrough.

In some embodiments, the first and/or second drive wheel can be rotatable connected to a first support member (e.g., in a fixed and/or selectively adjustable relationship or distance). The drive wheel(s) can be replaceable by one or more drive wheels of different sizes (e.g., radius, circumference, recessed circumference surface area, etc.). Accordingly, the assembly can be configurable to receive, accommodate, and/or bend surgical rods having a variety of shapes, sizes, etc. The first support member can also be pivotably attached to a second support member (e.g., at one or more attachment interfaces). The guide element can be (rotatably or non-rotatably) attached to the second support member such that movement of the second support member relative to the first support member (e.g., pivoting at the interface(s)) causes movement of the guide element relative to one or more of the first drive wheel and second drive wheel.

In at least one embodiment, one or more of the first and second support member can include an elongated arm (and/or handle). The elongated arm can extend from a pivotable attachment interface (i.e., pivot point and/or fulcrum) so as to function as a lever in some embodiments. For instance, in certain embodiments, the assembly can have a scissor-like configuration, wherein each of the first and second support members can include an elongated arm extending from a pivot point. The first drive wheel, second drive, and guide element can be attached to one or more of the support members on an opposite side of the fulcrum such that a mechanical advantage can be achieved in actuating the elongated arms about the fulcrum. For instance, the second drive wheel can be attached to the first support member, the guide element can be attached to the second support member, and the first drive wheel can be attached at the pivot point between the first and second support members. Accordingly, movement of the elongated arms can cause movement of the guide element relative to the second drive wheel.

In an alternative embodiment, one of the first and second support members can include an elongated arm and the other of the first and second support member can comprise a base. The elongated arm can optionally comprise an articulated arm assembly in certain embodiments. Moreover, the articulated arm assembly can be attached to the base such that a mechanical advantage can be achieved in moving the guide element relative the one or more of the first and second support members. For instance, the arm assembly can comprise a plurality of connected arm segments. A first, elongated arm segment can be pivotably connected to the base at a first interface (e.g., at a first end of the arm segment). The first arm segment can also be connect to a second arm segment (e.g., at a connection interface between the first end and opposing second end) such that the second arm segment moves as the elongated first arm segment is moved (i.e., pivoted about the first interface). Additional arm segments can also be attached (e.g., in series) such that the arm segments move in concert one with another. One or more of the additional arm segments can be attached to the base at a second interface (e.g., to provide additional support and/or pivot point(s) for the arm assembly).

In at least one embodiment, the guide element (or first and/or second drive wheels) can be attached to one of the additional arm segments (e.g., a last in the series of arm segments). The first and/or second drive wheels (or guide wheel), on the other hand, can be attached to the base such that the first drive wheel, second drive wheel, and guide element are disposed adjacent to one another. Actuation of the arm assembly, via pivotable movement of the elongated first arm segment, can cause the guide element to move relative to the first and/or second drive wheels, or vice versa. The arm assembly can further provide a mechanical advantage in moving the guide element relative to the first and/or second drive wheels, or vice versa. Accordingly, a first force applied to the elongated arm segment can cause a second force to be applied to a surgical rod disposed between the first and second drive wheels and between the guide element and one or more of the first and second drive wheels, the second force being sufficient to bend the surgical rod to a first curvature or radius of curvature. The arm assembly can be further actuated to bend the surgical rod to a second curvature or radius of curvature, third curvature or radius of curvature, and so forth.

Regardless of the specific embodiment or configuration of the assembly, with the surgical rod bent to the first (or second, etc.) curvature or radius of curvature in the closed assembly, the first drive wheel, second drive wheel, and/or guide element can be rotated to advance the surgical rod through the assembly such that the surgical rod is bent to the curvature or radius of curvature along a length thereof. The assembly need not be re-opened (e.g., into the open configuration and/or non-clamping position) to effectuate and/or accomplish bending the surgical rod along a length thereof. Thus, unlike existing rod benders that form a first bend at a first point on the rod, and then must be opened in order to move the rod to a new position within the bender before bending the rod at a second point, embodiments of the present disclosure can remain in the closed configuration and/or clamping position and (uniformly) bend the surgical rod along the length as it advances through the assembly. Thus, instead of a plurality of point-bends, as in existing rod benders, embodiments of the present disclosure can provide a consistent bend along the length of the surgical rod.

In addition, certain embodiments may be described with reference to one or more metals or metal materials. For instance, the surgical rod, assembly, or one or more components thereof can comprise or be formed of a metal or metal material. As used herein, the term "metal" refers to a material that comprises an elemental metal or metal alloy, blend, or combination. Certain embodiments may also refer to heat and/or smoke distribution and/or circulation. It will be appreciated that such forms of directing and/or using heat and/or smoke can include active distribution and/or circulation and/or passive distribution and/or circulation.

It is further to be understood that some of the drawings included herewith, and which are referenced herein, are diagrammatic, schematic, and other representations of example embodiments, and are not limiting on the present disclosure. Moreover, while various drawings are provided at a scale that is considered functional for some embodiments, the drawings are not necessarily drawn to scale for all contemplated embodiments. No inference should therefore be drawn from the drawings as to the necessity of any scale. Rather, the proportionality, scale, size, shape, form, function, and/or other feature of the disclosed embodiments can be altered without necessarily departing from the scope of this disclosure (unless such feature is expressly described herein as essential).

Furthermore, as indicated above, in the exemplary embodiments illustrated in the figures, like structures will be provided with similar reference designations, where possible. Specific language will be used herein to describe the exemplary embodiments. Nevertheless it will be understood that no limitation of the scope of the disclosure is thereby intended. Rather, it is to be understood that the language used to describe the exemplary embodiments is illustrative only and is not to be construed as limiting the scope of the disclosure (unless such language is expressly described herein as essential).

Alterations and further modifications of the inventive features illustrated herein, and additional applications of the principles illustrated herein, which would occur to one skilled in the relevant art and having possession of this disclosure, are to be considered within the scope of this disclosure. Unless a feature is described as requiring another feature in combination therewith, any feature herein may be combined with another feature of a same or different embodiment disclosed herein. Furthermore, various well-known aspects of illustrative systems, methods, apparatus, and the like are not described herein in particular detail in order to avoid obscuring aspects of the example embodiments.

Figure 5:
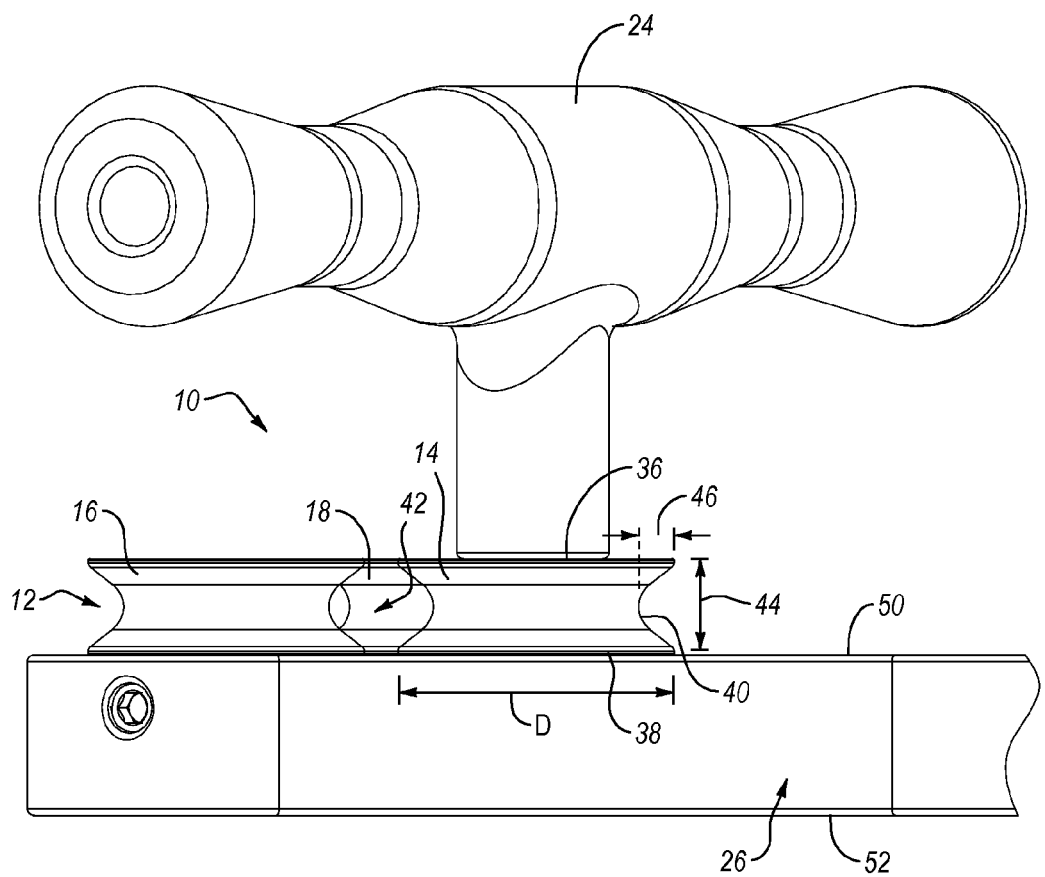
FIG. 5 is a detailed, side elevation view thereof.

Reference will now be made the figures to describe specific embodiments of the present disclosure. FIGS. 1A and 1B illustrate a rod bending assembly 10 incorporating certain aspects of the present disclosure. Rod bending assembly 10 includes a drive wheel assembly 12 having a first drive wheel 14, a second drive wheel 16 disposed adjacent to first drive wheel 14, and a guide element 18 disposed adjacent to first drive wheel 14 and second drive wheel 16. As depicted in FIG. 5, first drive wheel 14, second drive wheel 16, and guide element 18 each have a pulley wheel-type configuration, with an upper wheel surface 36, an opposing lower wheel surface 38, and a recessed circumferential surface 40 extending therebetween. Recessed circumferential surface 40 extends uniformly and entirely around each of first drive wheel 14, second drive wheel 16, and guide element 18. However, alternative embodiments can include a non-uniform and/or partial circumferential surface. Recessed circumferential surface 40 can have and/or comprise any suitable taper angle (e.g., relative to upper wheel surface 36 and/or lower wheel surface 38). In at least one embodiment, the taper angle can be approximately 75 degrees. It will be appreciated, however, that any suitable taper angle between about 1 degree and about 179 degrees is contemplated herein.

Recessed surface 40 is configured to receive and/or accommodate one or more sizes (e.g., gauge, diameter, radius, circumference, etc.) and/or shapes of surgical rods. For instance, the rounded, concave, recessed surfaces 40 illustrated in FIG. 5, or taper angle thereof, can be configured to receive surgical rods having a rounded (e.g., substantially circular) cross-sectional configuration in any suitable range of diameters that fit through a gap 42 between first drive wheel 14 and second drive wheel 16. The size of gap 42 is determined, at least in part by a recess height 44 and/or recess depth 46, as well as the distance between first drive wheel 14, second drive wheel 16, and optionally guide element 18. The distance between components can be altered by changing an attachment point in some embodiments. In other embodiments, however, the distance between components is adjusted by substitution of the components for ones having a smaller diameter D. Thus, assembly 10 and/or drive wheel assembly 12 thereof can be reconfigured to receive and/or accommodate larger surgical rods by replacing first drive wheel 14, second drive wheel 16, and optionally guide element 18 with components having a larger recess height 44, a larger recess depth 46, and/or a small diameter D.

Returning to FIGS. 1A and 1B, rod bending assembly 10 also includes a support assembly 26 having a first support member 28 and a second support member 30 pivotably attached to first support member 28 at an interface 32. Interface 32 can comprise a fulcrum or pivot point about which first and second support members 28 and 30 can be actuated and/or otherwise moved. As illustrated in FIGS. 1A and 1B, first drive wheel 14 is rotatably connected to first support member 28 and second support member 30 at interface 32. Thus, a rotational axis of first support member 28 can comprise a pivot point of assembly 10. Second drive wheel 16 is rotatably attached to first support member 28 and guide element 18 is rotatably attached to second support member 30. As depicted in FIG. 1A, drive wheel assembly 12 and/or first drive wheel 14, second drive wheel 16, and guide element 18 thereof are attached and/or disposed at an upper side (surface) 50 of support assembly 26.

Figure 3:
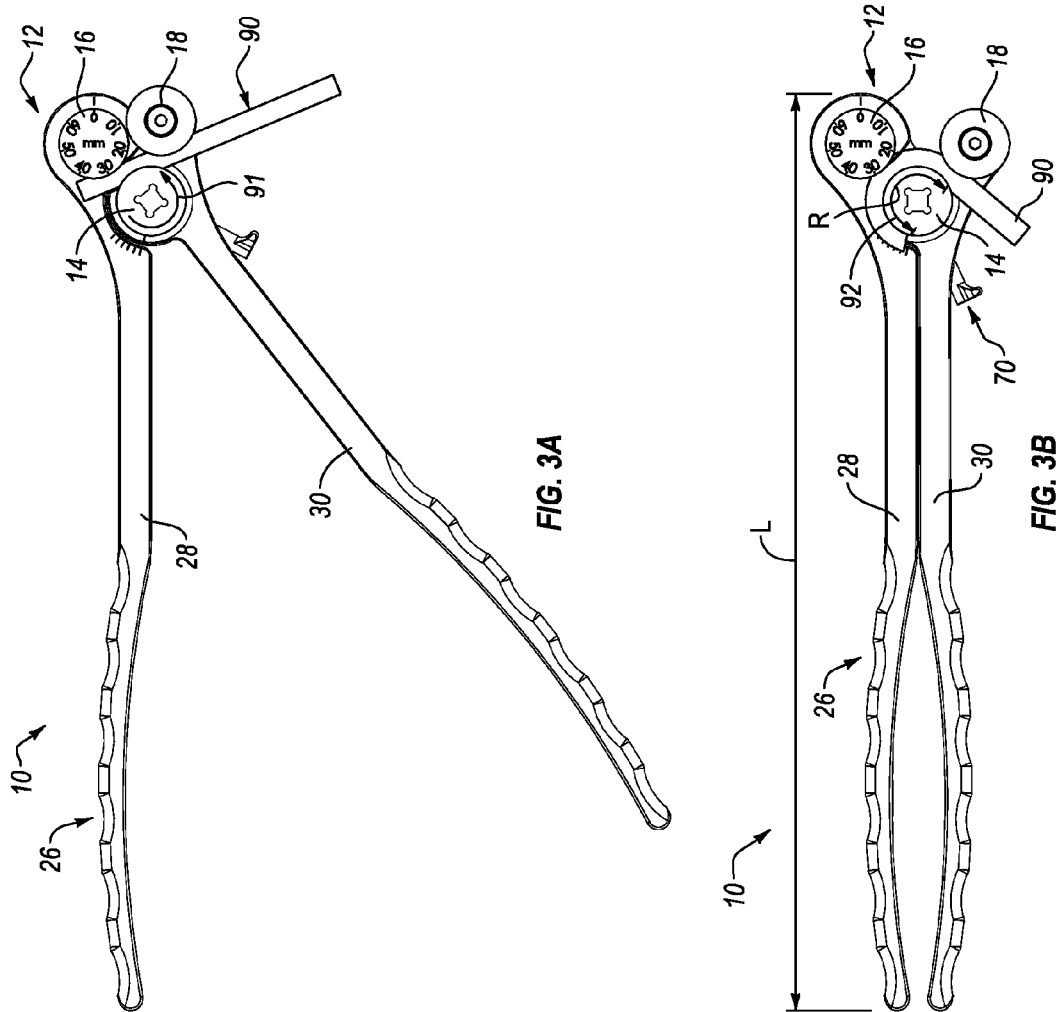
FIG. 3A is a top plan view thereof in an open configuration.
FIG. 3B is a top plan view thereof in an closed configuration and with a bend surgical rod disposed therein.

First and second support members 28 and 30 each comprise an elongated arm having a gripping element 34 disposed at a first end thereof distal to interface 32. It will be appreciated that assembly 10 can be configured to be supported (entirely) in or by the hands of a user. For instance, as illustrated in FIG. 3B, assembly 10 can have a length L suitable for hand-held operation. Thus, assembly 10 can comprise a hand-held rod bender assembly. In other embodiments, however, assembly 10 can comprise a support structure-mounted rod bending assembly. Thus, length L (and/or other measurement of assembly 10) can be suitable for support structure-mounted operation without necessarily departing from the scope of this disclosure.

Assembly 10 also includes a means for rotating first drive wheel 14. For instance, assembly 10 includes a drive handle 24 connected to first drive wheel 14 such that rotation of drive handle 24 cause rotation of first drive wheel 14. Assembly 10 also includes a means for rotating second drive wheel 16 via rotating first drive wheel 14. For instance, assembly 10 includes a gear assembly 20 that includes a plurality of gear members 22. As depicted in FIG. 1B, a first gear member 22a is axially connected to first drive wheel 14 and a second gear member 22b is axially connected to second drive wheel 16 on an opposing lower side 52 of support assembly 26. Gear members 22a and 22b have interlocking teeth 23 disposed about the circumference thereof. Accordingly, rotation of first gear member 22a causes rotation of second gear member 22b, and vice versa. Thus, rotation of first drive wheel 14 via drive handle 24 causes rotation of first gear member 22a, causing rotation of second gear member 22b, which causes rotation of second drive wheel 16. As indicated above, the means for rotating can also or alternatively include a crank, a cam, a lever, a pulley, a pump, a hydraulic, and/or any suitable mechanism for coordinating rotation of two or more components.

Guide element 18, however, does not include a gear member 22 or other driving mechanism. Instead, guide element 18 is freely rotatable about an axle element 54. As illustrated more fully in FIG. 2, first and second drive wheels 14 and 16 are axially connected to first and second gear members 22a and 22b, respectively, by a first axle element 56 (extending from first and second drive wheels 14 and 16, respectively) and a second axle element 58 (extending from first and second gear members 22a and 22b, respectively). First and second axle elements 56 and 58 form a post-and-socket connection that is secured and/or maintained by one or more fasteners 60 extending therethrough. For instance, one or more of first and second axle elements 56 and 58 can have a (threaded) receiving element 57 for (threadedly) receiving (threaded) fastener 60. A set screw 61 can also substantially prevent and/or inhibit retraction and/or removal of fastener 60 from the post-and-socket connection of first and second axle elements 56 and 58 in some embodiments. In other embodiments, (the opening of) receiving element 57 can be turned so as to substantially prevent and/or inhibit retraction and/or removal of fastener 60 from the post-and-socket connection of first and second axle elements 56 and 58.

Assembly 10 and/or first drive wheel 14 thereof can also include an attachment mechanism for connecting drive handle 24 to first drive wheel 14. For instance, first drive wheel 14 includes a receiving element (or socket) 62. An attachment element 64 can be received by (e.g., at least partially within) receiving element 62 such that drive handle 24 can be connected to first drive wheel 14. For instance, drive handle 24 also includes a receiving element (or socket) 66 configured to receiving a portion of attachment element 64. In an alternative embodiment, attachment element 64 can extend from drive handle 24 or first drive wheel 14.

Returning briefly to FIGS. 1A and 1B, assembly 10 also includes a securing mechanism 70, by which assembly 10, drive wheel assembly 12, support assembly 26, and/or components thereof can be secured in one or more configurations and/or clamping positions. For instance, as depicted in FIGS. 1A-1B and 2A-2B, securing mechanism 70 comprises an elongated securing element 72 extending through second support member 30 and biased by a biasing element 74 towards a receiving element 76 such that a first end 71 of securing element 72 selectively interacts with receiving element 76 when securing element 72 is in a forward position. A second end 73 of securing element 72 can be connected to a gripping element 78 so as to provide a handle by which securing element 72 can be pulled away from receiving element 76 into a retracted position. In the retracted position, first support member 28 can move (pivotably) towards and/or away from second support member 30 (about interface 32).

In the forward position, first support member 28 can move (pivotably) towards second support member 30 (about interface 32). However, the interaction between securing element 72 and receiving element 76 in the forward position substantially prevents and/or inhibited first support member 28 from moving (pivotably) away from second support member 30 (about interface 32). Furthermore, securing mechanism 70 can comprise a ratcheting mechanism, wherein biasing element 74 forces securing element 72 into the slots 77, respectively, of receiving element 76 as first and second support members 28 and 30 are moved (pivotably) towards each other. Accordingly, as assembly 10 is progressively closed into each of the plurality of clamping positions, securing mechanism 79 can substantially prevent and/or inhibit assembly 10 from inadvertently opening when securing element 72 interacts with receiving element 76.

Figure 4:
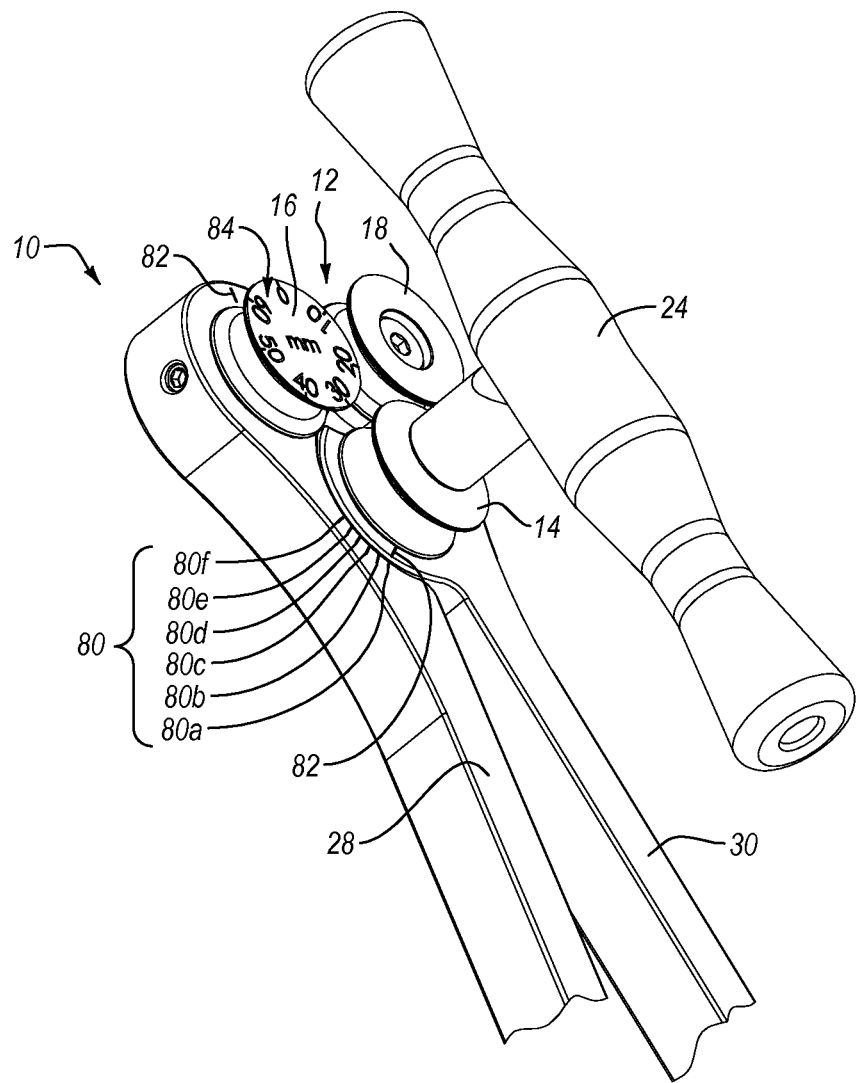
FIG. 4 is a detailed view thereof.

It will be appreciated that each of the slots 77 of receiving element 76 can represent a distinct clamping position in which a surgical rod advancing through assembly 10 will be bent to a specific curvature or radius of curvature. Furthermore, as illustrated in FIG. 4, each of the slots 77 of receiving element 76 can be marked on upper surface 50 of first support member 28 by a marking element 80 disposed thereon, with a clamping position indicator 82 disposed on upper surface 50 of second support member 30, such that the position of securing element 72 within one of slots 77 of receiving element 76 is indicated visually thereby. Accordingly, the position of clamping position indicator 82 relative to marking element 80 (or markings 80a-80f thereof) indicates the clamping position of assembly 10 and/or drive wheel assembly 12, as well as the specific curvature or radius of curvature to which the surgical rod will be bent as it advances through assembly 10 and/or drive wheel assembly 12, as discussed in further detail below.

FIGS. 3A and 3B illustrate an exemplary method of operation of assembly 10 according to an embodiment of the present disclosure. As depicted in FIG. 3A, for instance, assembly 10, drive wheel assembly 12, and/or support assembly 26 can be disposed in an open configuration and/or non-clamping position, in which first and second support members 28 and 30 are moved (pivotably) away from one another such that guide element 18 is disposed against and/or adjacent to second drive wheel 16. A surgical rod 90 can thereby be inserted between first and second drive wheels 14 and 16, and between first drive wheel 14 and guide element 18 (e.g., without being bent or otherwise (substantially) altering the linear configuration of surgical rod 90.

As depicted in FIG. 3B, assembly 10, drive wheel assembly 12, and/or support assembly 26 can also be disposed in a closed configuration and/or clamping position, in which first and second support members 28 and 30 are moved (pivotably) towards each other such that guide element 18 is moved away from second drive wheel 16. Surgical rod 90 disposed between first and second drive wheels 14 and 16, and between first drive wheel 14 and guide element 18 is thereby bent to a first curvature or radius of curvature R. Securing mechanism 70 can secure assembly 10, drive wheel assembly 12, and/or support assembly 26 in the closed configuration and/or clamping position.

It will be appreciated that while FIGS. 3A and 3B depict a fully opened configuration (corresponding to marking 80a of FIG. 4) and a fully closed configuration (corresponding to marking 800, respectively, that various intermediate closed configurations (corresponding to markings 80b-80e) are also available. As indicated above, for instance, each of the slots 77 of receiving element 76 (see FIG. 4) can represent a distinct clamping position in which a surgical rod disposed therein will be bent to a specific curvature or radius of curvature (e.g., by first and second drive wheels 14 and 16, and by first drive wheel 14 and guide element 18). The fully opened configuration depicted in FIG. 3A can correspond to and/or produce a curvature substantially equal to and/or approaching zero (i.e., the smallest curvature), or radius of curvature substantially equal to and/or approaching infinity (i.e., the largest radius of curvature). Thus, a surgical rod disposed therein may be substantially linear and/or unbent in the fully opened configuration (or non-clamping position).

The fully closed configuration depicted in FIG. 3B, on the other hand, can correspond to and/or produce the largest curvature (a curvature greater than that of the fully opened position) and/or the smallest radius of curvature (a radius of curvature less than that of the fully opened position). In some embodiments, the smallest radius of curvature will be equal to the internal radius of first and second drive wheels 14 and 16 (e.g., between 5 mm and 30 mm). It will be appreciated, however, that any suitable internal wheel radius and/or radius of curvature, including those less than 5 mm and/or greater than 30 mm, are also contemplated herein. Each clamping position and/or configuration between the fully opened configuration and the fully closed configuration (e.g., corresponding to markings 80b-80e of FIG. 4) can correspond to and/or produce a different curvature and/or radius of curvature. In at least one embodiment, the radius of curvature can become progressively smaller as assembly 10, drive wheel assembly 12, and/or support assembly 26 is progressively closed and/or moved through clamping position indicated by markings 80a-80f, respectively.

Regardless of clamping position and/or configuration, rotation of first drive wheel 14 in a first (counter-clockwise) direction 91 can advance surgical rod 90 through assembly 10 and/or drive wheel assembly 12 such that surgical rod 90 is bent (uniformly) to the specific (first) curvature or radius of curvature R along a first length 92. It will also be appreciated that the measurement of first length 92 can also be indicated visually on the surface of assembly 10. For instance, as depicted in FIG. 4, drive wheel 16 can have a plurality of length markings 84 disposed thereon. As drive handle 24 is rotated, drive wheels 14 and 16 rotate in concert to advance the surgical rod therethrough. As drive wheels 14 and 16 rotate, the position of length markings 84 (e.g., relative to the surgical rod) can indicate how far through assembly 10 and/or drive wheel assembly 12 the surgical rod has advanced. Accordingly, a user can determine when to stop rotating drive handle 24, when to adjust the clamping position of assembly 10 and/or drive wheel assembly 12, and/or when to open assembly 10 and/or drive wheel assembly 12 (e.g., to remove the surgical rod).

It will be appreciated that embodiments of the present disclosure provide a significant advantage over existing device that produce a plurality of bent segments in a surgical rod by clamping the device on a first portion of the rod, opening the device, moving the rod, clamping down on a second portion of the rod, and so forth. Embodiments of the present disclosure are adapted for clamping down on a first portion of a surgical rod, and advancing the rod a first distance through the assembly to produce a smooth curve and/or radius of curvature along a length of the rod. The assembly can also be adjusted to alter the curvature or radius of curvature at a location to which the rod has been advanced. The altered curvature or radius of curvature can be larger or smaller that the first curvature or radius of curvature. For instance, at a second location (e.g., at the end of the first length opposite the first location), the radius of curvature can be increased (e.g., by partially opening the assembly) or decreased (e.g., by further closing or clamping the assembly).

The surgical rod can, thus, be custom-prepared for implantation into a patient. The patient may be human or other species of animal. In particular, a custom surgical implant can be formed of the bent surgical rod and the implant can be implanted at least partially within the body of a patient. The implant procedure can include affixing the bent surgical rod and/or implant to a skeletal component of the patient in some embodiments.

Figure 6A:
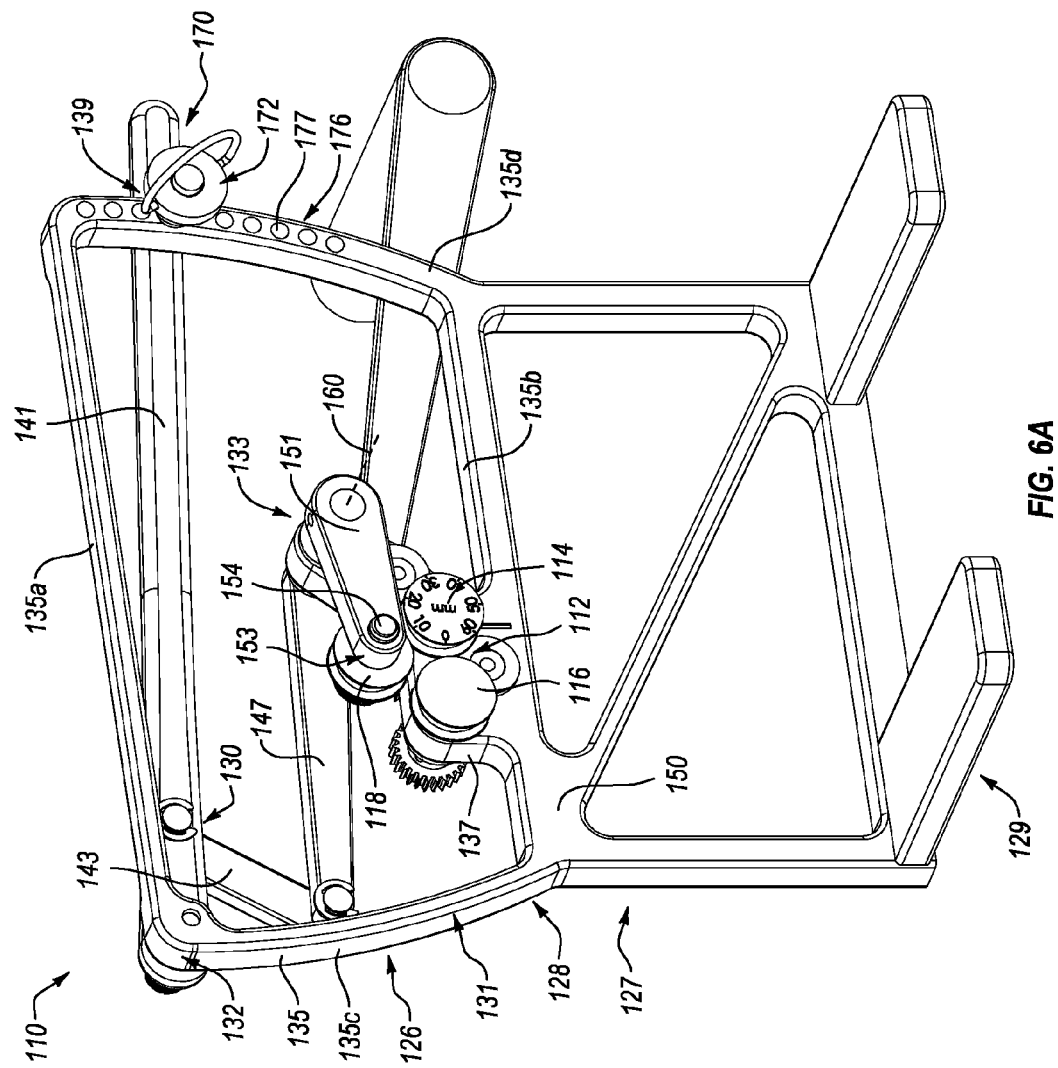
FIG. 6A is a top, front perspective view of an articulating surgical rod bender assembly according to another embodiment of the present disclosure.

Depicted in FIGS. 6A-8B is an alternative embodiment of a rod bending assembly 110 incorporating certain aspects of the present disclosure. Rod bending assembly 110 can provide advantages over existing devices similar to those described in reference to rod bending assembly 10. Likewise, rod bending assembly 110 can comprise components similar to those described in relation to rod bending assembly 10 and like-names have been used to indicate like structure or structure that performs like function(s). For instance, rod bending assembly 110 includes a drive wheel assembly 112 having a first drive wheel 114, a second drive wheel 116 disposed adjacent to first drive wheel 114, and a guide element 118 disposed adjacent to first drive wheel 114 and second drive wheel 116. It will be appreciated that first drive wheel 114, second drive wheel 116, and guide element 118 can have the same configuration and/or structural elements as first drive wheel 14, second drive wheel 16, and guide element 18, above. For instance, first drive wheel 114, second drive wheel 116, and guide element 118 each have a pulley wheel-type configuration as described previously. As depicted in FIG. 6A, drive wheel assembly 112 and/or first drive wheel 114, second drive wheel 116, and guide element 118 thereof are attached and/or disposed at a first side 150 of a support assembly 126 (or component thereof).

Rod bending assembly 110 also has various features that are different than those illustrated in rod bending assembly 10. For instance, unlike rod bending assembly 10, support assembly 126 of rod bending assembly 110 includes a first support member 128 and a second support member 130 pivotably attached to first support member 128 at a first interface 132, a second interface 133, and a third interface 139. As illustrated in FIG. 6A, first support member 128 comprises a base having a lower mounting element 127 and an upper support element 131 extending (vertically upward) from mounting element 127. Mounting element 127 can also include means for mounting rod bending assembly 110 to a support structure. For instance, one or more flanges 129 can extend (e.g., perpendicularly) from mounting element 127 and can be mounted to a surface of a support structure, such as a table, wall, etc.

As further illustrated in FIG. 6A, support element 131 comprises an encircling frame element 135, having an upper frame member 135a, a lower frame member 135b, a first side frame member 135c extending between upper frame member 135a and lower frame member 135b, and an opposing second side frame member 135d extending between upper frame member 135a and lower frame member 135b opposite first side frame member 135c. Support element 131 can also include an attachment element 137 extending from and/or into frame element 135. For instance, as depicted in FIG. 6A, attachment element 137 extends and/or projects from lower frame member 135b, into the space bound by frame element 135. In other embodiments, however, support element 131 need not comprise an outer frame and an inner attachment element. For instance, support element 131 can comprise alternatively comprise a substantially solid and/or uniform member (e.g., sheet metal) having upper, lower, and side edges instead of frame elements. Such a support element can have other components similar or identical to those depicted in the figures.

Figure 6B:
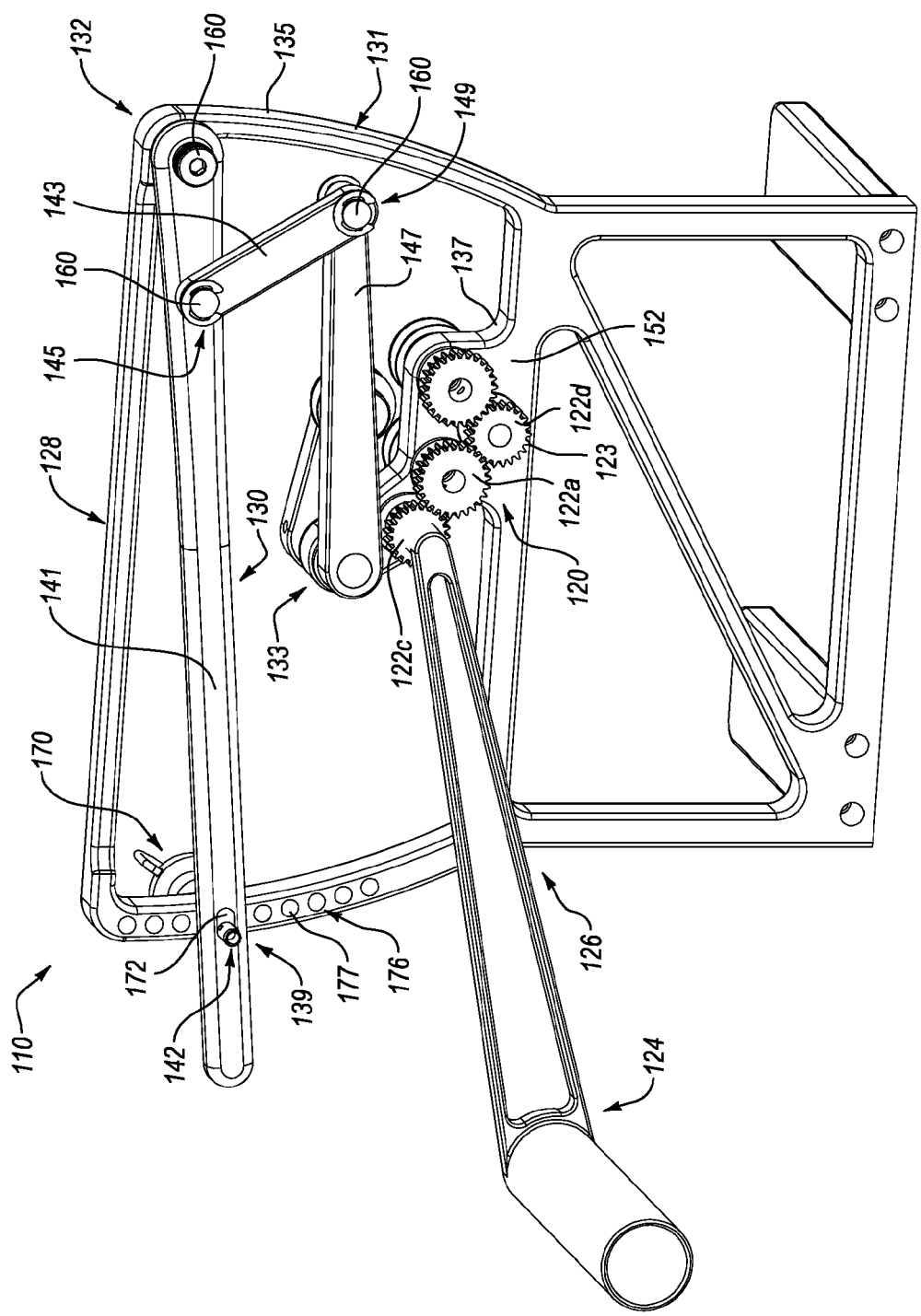
FIG. 6B is a top, rear perspective view thereof.

As illustrated in FIG. 6B, second support member 130 comprises an articulated arm assembly comprising a first, elongated arm segment 141 pivotably connected to support element 131 and/or frame element 135 thereof at first interface 132 via a fastener 160. First arm segment 141 is also selectively connectable to support element 131 and/or frame element 135 thereof at third interface 139, where a securing mechanism 170 attached to and/or connected between first arm segment 141 and support element 131 and/or frame element 135 thereof secures first arm segment 141 in a plurality of positioned represented by a plurality of slots 177 of a receiving element 176. Each slot 177 can have a numeric value or other indicator (not shown) associated therewith (e.g., printed or laser cut unto support element 131 and/or frame element 135 thereof) to indicate a specific setting and/or curvature or radius of curvature to which drive wheel assembly 112 is configured. Securing mechanism 170 also comprises a securing element 172 selectively and reversibly securable to and/or within receiving element 176 and/or the plurality of slots 177 thereof. In particular, securing element 172 can be insertable through and/or into a slot 177 and an opening 142 in first arm segment 141.

As illustrated in FIGS. 6A and 6B, the articulated arm assembly of second support member 130 also comprises a second arm segment 143, a third arm segment 147, and a fourth arm segment 151 (connected in series). A first end of second arm segment 143 is connected to first arm segment 141 at a connection interface 145 via a fastener 160. Connection interface 145 can be disposed and/or positioned between first interface 132 and third interface 139 (or between opposing ends of first arm segment 141). A first end of third arm segment 147 is connected to an opposing second end of second arm segment 141 at a connection interface 149 via a fastener 160. A first end of fourth arm segment 151 is connected to an opposing second end of third arm segment 147, each of which is connected to support element 131 and/or attachment element 137 thereof at second interface 133 via a fastener 160. An opposing second end of fourth arm segment 151 is connected to guide element 118 at a connection interface 153 via an axle element 154.

As illustrated in FIGS. 8A and 8B, first arm segment 141 is selectively moveable (e.g., pivotable, actuatable, etc.) between a first position corresponding to a first slot 177a of receiving element 176 and a second position corresponding to a second slot 177j. It will be appreciated that each of the plurality of slots 177a-177j corresponds to a different position to which first arm segment 141 is selectively moveable and/or at which first arm segment 141 is selectively securable via securing mechanism 170. As the second end of first arm segment 141 is moved (downward) from the first position corresponding to first slot 177a to the second position corresponding to second slot 177j, the first end of first arm segment 141 pivots about first interface 132. Second arm 143 is moved (downward) thereby, which causes a corresponding movement of the first end of third arm segment 147, causing the opposing second end of third arm segment 147 to pivot about second interface 133, which causes a corresponding pivoting of the first end of fourth arm 151 about connection interface 153. As fourth arm 151 pivots about connection interface 153, the opposing second end of fourth arm 151 is moved (downward), causing guide element 118 to move toward first and second drive wheels 114 and 116, as illustrated in FIG. 8B. Accordingly, FIG. 8B illustrates a first closed configuration and/or clamping position of assembly 110, drive wheel assembly 112, and/or support assembly 126.

Figure 7:
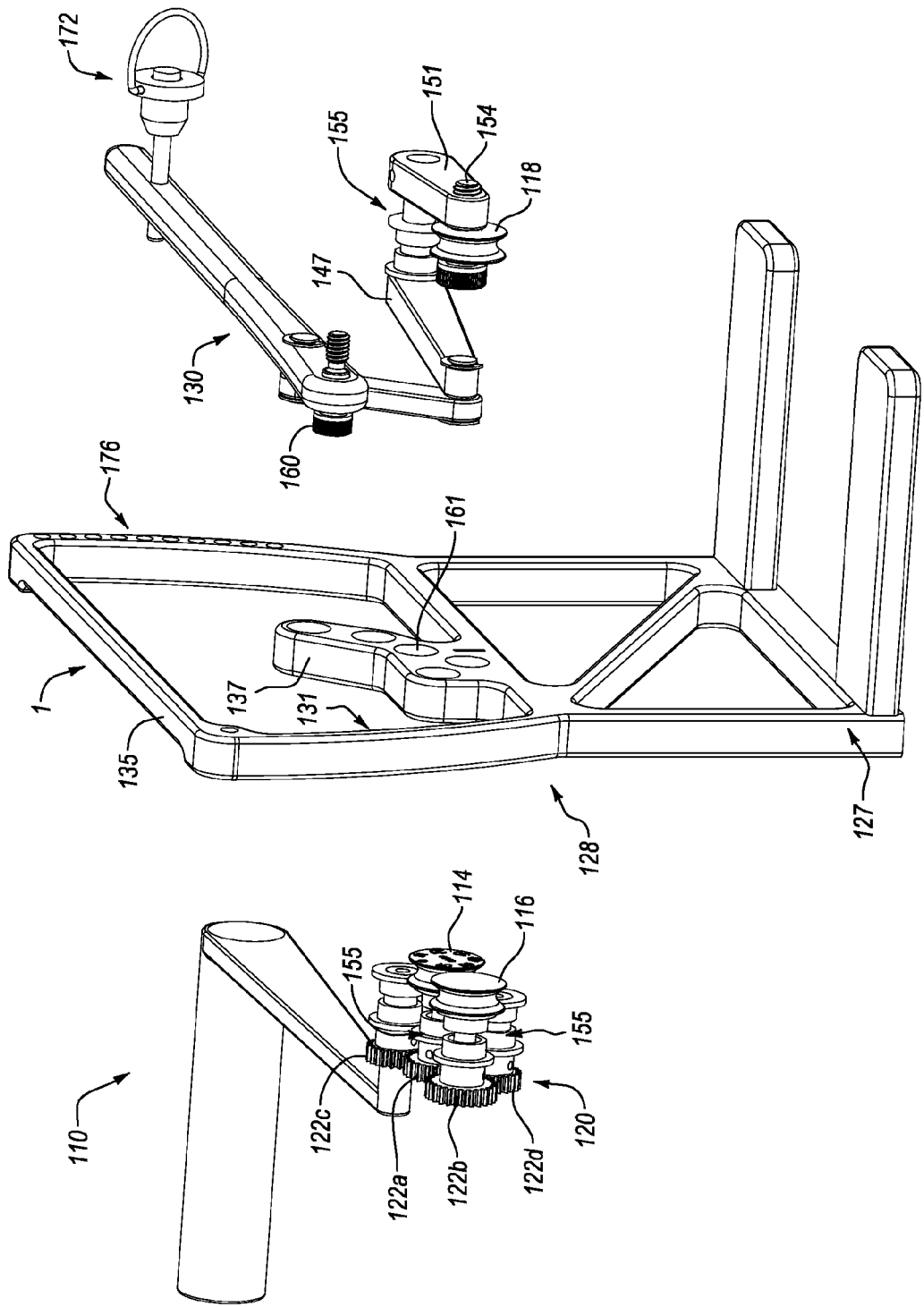
FIG. 7 is an exploded view thereof.

As illustrated in FIGS. 6B and 7, assembly 110 also comprises a means for rotating second drive wheel 116 via rotating first drive wheel 114. Specifically, assembly 110 comprises a gear assembly 120 (rotatably) connected to support assembly 126, first support member 128 and/or attachment element 137 thereof. Gear assembly 120 comprises a first gear member 122a axially connected to first drive wheel 114 and a second gear member 122b axially connected to second drive wheel 116 on an opposing second side 152 of support assembly 126, first support member 128, and/or attachment element 137. Gear assembly 120 also comprises a third gear member 122c axially connected to support assembly 126, first support member 128, and/or attachment element 137, and circumferentially connected to first gear member 122a. Gear assembly 120 also comprises a fourth gear member 122d axially connected to support assembly 126, first support member 128, and/or attachment element 137, and circumferentially connected to first gear member 122a and second gear member 122b.

Gear assembly 120 can also be configured to provide a mechanical advantage in rotating the second drive wheel 116 via rotating the first drive wheel 114 (e.g., sufficient to effectuate the bending of the surgical rod along the length thereof). In one or more embodiments, for instance one or more gear members 122 can be sized so as to provide the mechanical advantage. For instance, third gear member 122c and/or fourth gear member 122d can be sized (or geared) relative to the size of first gear member 122a and/or second gear member 122b such that rotation of first gear member 122a and/or second gear member 122b becomes easier. Thus, the gear assembly and/or gear member(s) thereof can be "geared" to provide mechanical advantage.

Gear members 122a-122d each have interlocking teeth 123 disposed about the circumference thereof. Accordingly, rotation of any one of gear members 122a-122d causes rotation of the remaining of gear members 122a-122d. The means for rotating second drive wheel 116 via rotating first drive wheel 114 also comprises a drive handle 124 connected to third gear member 122c such that rotation of drive handle 124 causes rotation of third gear member 122c, which rotates first gear member 122a via teeth 123, causing rotation of first drive wheel 114. Rotation of first gear member 122a also rotates fourth gear member 122d via teeth 123, which rotates second gear member 122b via teeth 123, causing rotation of second drive wheel 116. As indicated above, however, the means for rotating can also or alternatively include a crank, a cam, a lever, a pulley, a pump, a hydraulic, and/or any suitable mechanism for coordinating rotation of two or more components.

As illustrated more fully in FIG. 7, guide element 118 is not axially connected to a gear member 122 or other driving mechanism. Instead, guide element 118 is freely rotatable about axle element 154, which extends into and/or through fourth arm segment 151. First and second drive wheels 114 and 116 are axially connected to first and second gear members 122a and 122b, respectively, by axle elements 155. First support member 128 and/or attachment element 137 thereof include a plurality of through holes or axle openings 161 (through which various components of assembly 110 can be attached and/or connected). For instance, axle elements 155 extend through openings 161 rotatably connecting first and second drive wheel 114 and 116 to first gear member 122a and 122b, respectively, rotatably connecting gear members 122c and 122d to first support member 128 and/or attachment element 137 thereof, and rotatably connecting third arm segment 147 to fourth arm segment 151.

Similar to assembly 10, assembly 110 can be operated to produce a custom bent surgical rod and/or implant incorporating the same. FIGS. 8A and 8B illustrate an exemplary method of operation of assembly 110 according to an embodiment of the present disclosure. Specifically, FIG. 8A illustrates an open configuration in which drive wheel assembly 112 is in a non-clamping position, in which second support member 130 and/or elongated first arm segment 141 thereof is moved and/or pivoted (upward) away from drive wheel assembly 112 such that guide element 118 is disposed away from first and second drive wheels 114 and 116. A surgical rod (not shown) can thereby be inserted between first and second drive wheels 114 and 116, and between guide element 118 and one of first and second drive wheels 114 and 116 (e.g., without being bent or otherwise (substantially) altering the linear configuration of surgical rod).

As depicted in FIG. 8B, assembly 110, drive wheel assembly 112, and/or support assembly 126 can also be disposed in a closed configuration and/or (first) clamping position, in which second support member 130 and/or elongated first arm segment 141 thereof is moved and/or pivoted (downward) towards drive wheel assembly 112 such that guide element 118 is disposed against and/or adjacent to first and second drive wheels 114 and 116. The surgical rod disposed between first and second drive wheels 114 and 116, and between guide element 118 and one of first and second drive wheels 114 and 116 is thereby bent to a first curvature or radius of curvature. Securing mechanism 170 can secure assembly 110, drive wheel assembly 112, and/or support assembly 126 in the closed configuration and/or clamping position. Furthermore, rotation of drive handle 124 in a first direction can advance the surgical rod through assembly 110 and/or drive wheel assembly 112 such that the surgical rod is bent (uniformly) to the first curvature or radius of curvature along a first length thereof. Specifically, rotation of drive handle 124 can cause simultaneous rotation of gear members 122 and first and second drive wheels 114 and 116.

Length markings 184 disposed on first drive wheel 114 can indicate how far through assembly 110 and/or drive wheel assembly 112 the surgical rod has advanced. It will be appreciated, however, that such length markings can be disposed elsewhere (e.g., second drive wheel 116 and/or gear assembly 120) without departing from the scope of this disclosure. One or more support markings 186 can provide a constant indicator of the rotation of length markings 184.

Thus, an illustrative method of implanting a custom surgical implant can include determining a desired curvature or radius of curvature for a surgical rod based on an anatomy of a patient, advancing at least a portion of the surgical rod through a rod bending assembly of the present disclosure (e.g., by rotating a first drive wheel of the rod bending assembly) so that the portion of the rod has the desired curvature or radius of curvature, and implanting the bent surgical rod at least partially within the body of the patient. The assembly can be configured as described in any of the above embodiments without departing from the scope of this disclosure.

The surgical rob can also be bent to the first curvature or radius of curvature at a first location by opening the rod bending assembly into a receiving position, inserting the surgical rod into the opened rod bending assembly so that the first drive wheel is located on a first side of the surgical rod and the second drive wheel is disposed on an opposing second side of the surgical rod, the guide element being disposed on the first side of the surgical rod or the second side of the surgical rod, and closing the rod bending assembly into a first clamping position so that the guide element and one or more of the first drive wheel and second drive wheel bend a portion of the surgical rod to the first curvature or radius of curvature. As indicated above, a portion of the drive assembly can be attached such that a mechanical advantage can be achieved in bending the surgical rod at one or more locations. For instance, the guide element can be attached to an articulating arm assembly that provides a leverage advantage sufficient to bend the surgical rod.

As further indicated above, the guide element, first drive wheel, and second drive wheel of the assembly can be disposed in a first configuration relative to one another such that the portion of the rod is bent to the desired curvature or radius of curvature as the portion passes between the first drive wheel and the second drive wheel and between the guide wheel and one of the first drive wheel and the second drive wheel. The method can also include determining a second curvature or radius of curvature, disposing the guide element, the first drive wheel, and the second drive wheel in a second configuration relative to one another (thereby bending the surgical rod to the second curvature or radius of curvature at a second location), and advancing a second portion of the surgical rod through the rod bending assembly by rotating the first drive wheel of the rod bending assembly so that the second portion of the rod has the second curvature or radius of curvature.

In at least some embodiments, the rotating step can include manually rotating a (drive) handle connected to the first drive wheel, the second drive wheel, and/or the means for rotating the second drive wheel via rotating the first drive wheel. The rod bending assembly can also be selectively secured in the first and/or second configurations and/or clamping positions as described above. The first and second drive wheels can also be rotated in concert (e.g., simultaneously) via a means for rotating the second drive wheel via rotating the first drive wheel. The means can comprise a gear assembly that provides a mechanical advantage sufficient to effectuate the bending of the surgical rod along the length thereof.

Figure 9A:
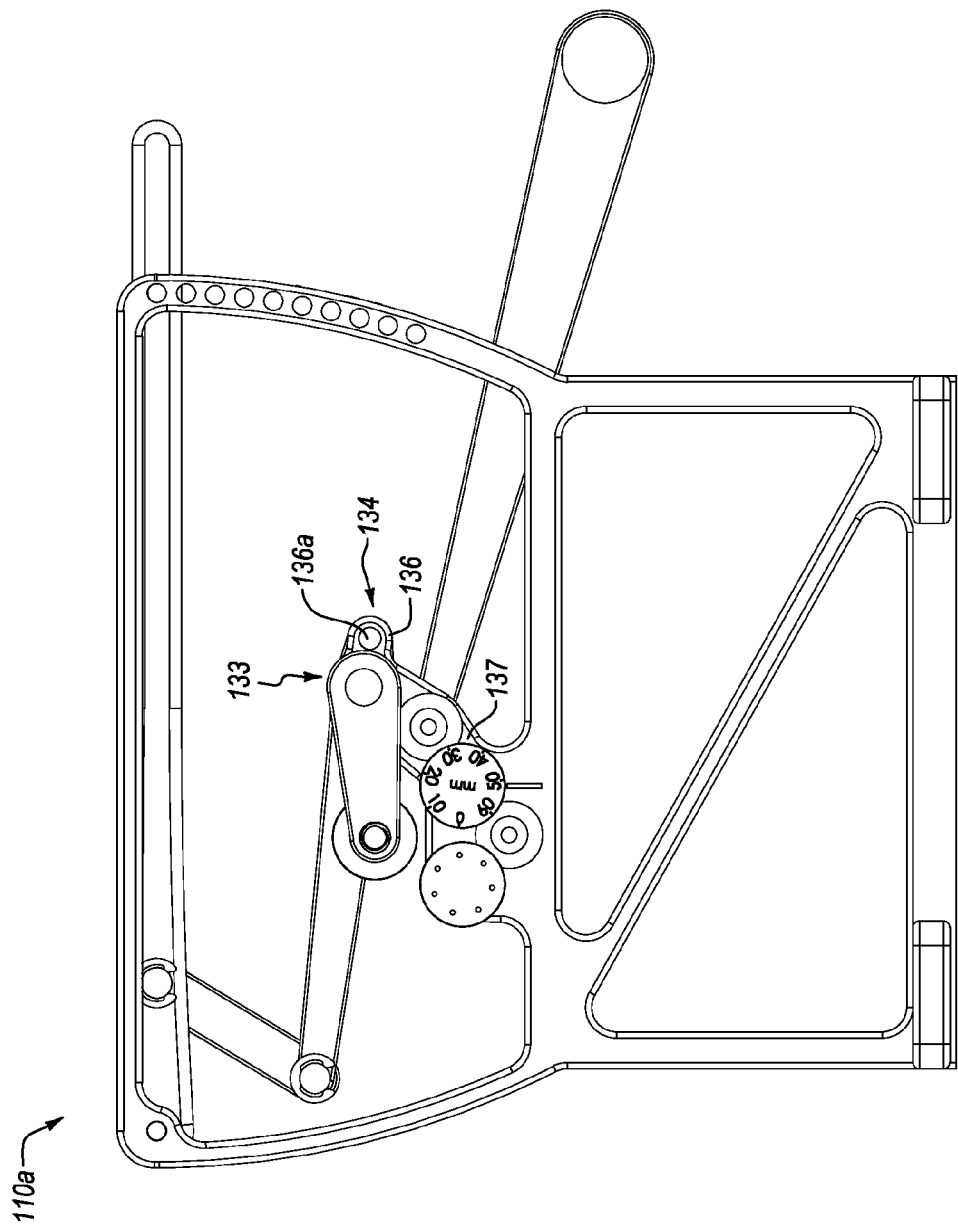
FIG. 9A is a front elevation view of an articulating surgical rod bender assembly in a first configuration according to yet another embodiment of the present disclosure.
Figure 9B:
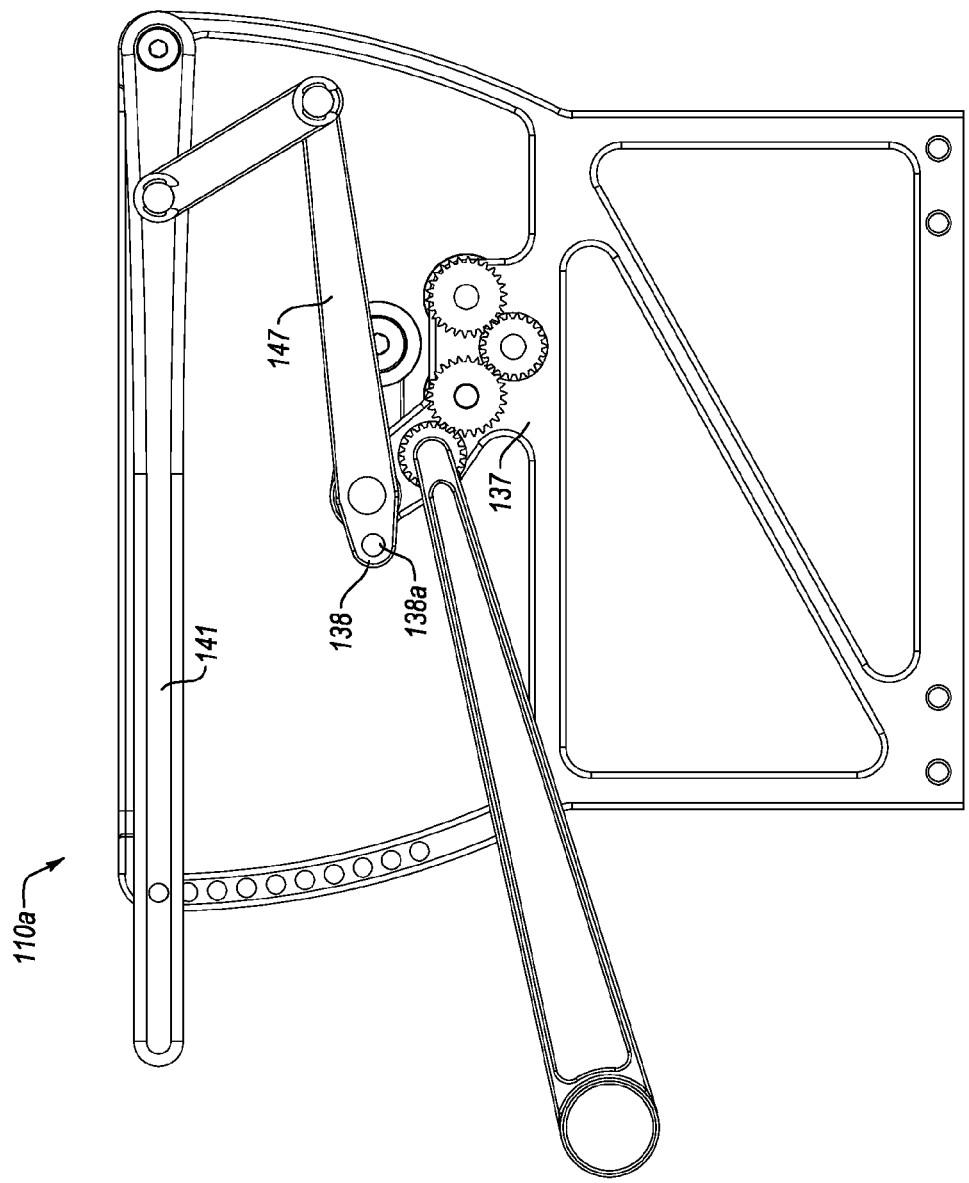
FIG. 9B is a front elevation view thereof in an open configuration.
Figure 10:
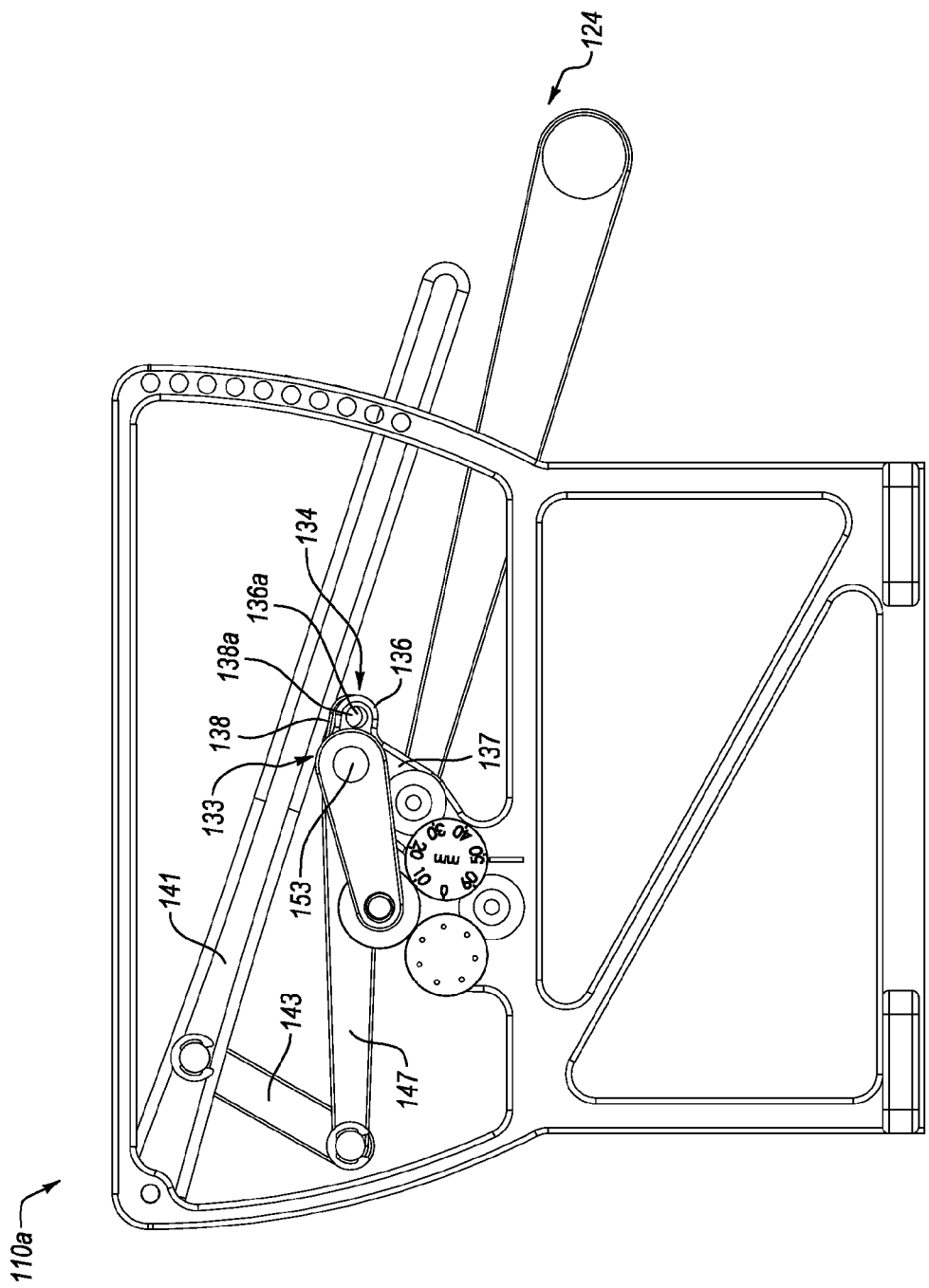
FIG. 10 is a front elevation view thereof in a second configuration.

FIGS. 9A-9B and 10 illustrate another embodiment of a rod bending assembly 110a incorporating certain aspects of the present disclosure. Rod bending assembly 110a can provide advantages over existing devices similar to those described in reference to rod bending assembly 10 and/or 110. Likewise, rod bending assembly 110a can comprise components similar to those described in relation to rod bending assembly 10 and/or 110 and like-names have been used to indicate like structure or structure that performs like function(s). Unlike rod bending assembly 10 and/or 110, however, rod bending assembly 110a includes a rod cutting assembly 134 adapted for altering the structural configuration of a surgical rod at one or more positions along the length thereof. In a typical embodiment, altering the structural configuration of the surgical rod comprises cutting, shearing, and/or severing the surgical rod at one or more positions along the length thereof. In alternative embodiments, however, altering the structural configuration of the surgical rod can comprise creasing, indenting, bending, perforating, pinching, or partially cutting through the surgical rod.

As illustrated in FIG. 9A, rod cutting assembly 134 comprises a first rod cutting element 136 extending from attachment element 137 (e.g., adjacent to second interface 133). First rod cutting element 136 has a receiving opening 136a extending therethrough. As illustrated in FIG. 9B, rod cutting assembly 134 also comprises a second rod cutting element 138 extending from the second end of third arm segment 147. Second rod cutting element 138 also has a receiving opening 138a extending therethrough. Second rod cutting element 138 is disposed adjacent to first rod cutting element 136. For instance, first rod cutting element 136 and second rod cutting element 138 can be aligned at an interface (e.g., adjacent to second interface 133) such that a negligible distance (e.g., less than 3 mm, less than 2 mm, less than 1 mm, less than 0.5 mm of space) is disposed between first rod cutting element 136 and second rod cutting element 138 and/or between receiving opening 136a and receiving opening 138a. In some embodiments, at least a portion of first rod cutting element 136 can be in direct contact with at least a portion of second rod cutting element 138 in some embodiments. In addition, first rod cutting element 136 and second rod cutting element 138 can be aligned such that when first arm segment 141 is disposed in the first position, as illustrated in FIGS. 9A and 9B, receiving opening 138a is substantially aligned with receiving opening 136a (e.g., such that a surgical rod can extend and/or pass through receiving opening 136a and receiving opening 138a at the same time).

As depicted in FIG. 10, however, when first arm segment 141 is disposed in the second position, receiving opening 138a is misaligned with receiving opening 136a (e.g., such that a surgical rod can extending and/or passing through receiving opening 136a and receiving opening 138a is altered structurally thereby). It will be appreciated that the mechanical force applied at the interface between first rod cutting element 136 and second rod cutting element 138 can be sufficient to alter the structural configuration of the surgical rod. However, in at least one embodiment, first rod cutting element 136 and/or second rod cutting element 138 can have a cutting edge adapted for focusing the applied force at a predetermined cutting point of the surgical rod.

Accordingly, in some embodiments, a surgical rod is inserted through receiving opening 136a and receiving opening 138a while first arm segment 141 is disposed in the first position. The surgical rod can be positioned such that the predetermined cutting point is disposed at the interface between first rod cutting element 136 and second rod cutting element 138 (or receiving opening 136a and receiving opening 138a thereof). First arm segment 141 is then actuated from the first position to (or towards) the second position, causing a corresponding movement of second arm segment 143, which causes third arm segment 147 to pivot about third interface 133, as described above. The pivoting of third arm segment 147 about third interface 133 causes the misalignment of receiving opening 136a and receiving opening 138a, which causes structural alteration of the surgical rod. It will be appreciated that the mechanical advantage provide and/or achieved by the articulated arm assembly in bending the surgical rod to a radius of curvature (described above) can similarly provide a mechanical advantage in altering the structural configuration of the surgical rod in the rod cutting assembly. The altered surgical rod can then be removed from rod cutting assembly 134. Those skilled in the art will appreciate that such alteration can take place before or after the surgical rod is bent by rod bending assembly 110a.

The foregoing detailed description makes reference to specific exemplary embodiments. However, it will be appreciated that various modifications and changes can be made without departing from the scope contemplated herein and as set forth in the appended claims. In particular, while illustrative exemplary embodiments in this disclosure have been more particularly described, the present disclosure is not limited to these embodiments, but includes any and all embodiments having modifications, omissions, combinations (e.g., of aspects across various embodiments), adaptations and/or alterations as would be appreciated by those in the art based on the foregoing detailed description. The limitations in the claims are to be interpreted broadly based on the language employed in the claims and not limited to examples described in the foregoing detailed description, which examples are to be construed as non-exclusive.

Moreover, any steps recited in any method or process described herein and/or recited in the claims may be executed in any order and are not necessarily limited to the order presented in the claims, unless otherwise stated (explicitly or implicitly) in the claims. Accordingly, the scope of the invention should be determined solely by the appended claims and their legal equivalents, rather than by the descriptions and examples given above.

It will also be appreciated that various features, members, elements, parts, and/or portions of certain embodiments of the present invention are compatible with and/or can be combined with, included in, and/or incorporated into other embodiments of the present invention. Thus, disclosure a certain features, members, elements, parts, and/or portions relative to a specific embodiment of the present invention should not be construed as limiting application or inclusion of said features, members, elements, parts, and/or portions to the specific embodiment. Rather, it will be appreciated that other embodiments can also include said features, members, elements, parts, and/or portions without necessarily departing from the scope of the present invention. Likewise, certain embodiments can include fewer features than those disclosed in specific examples without necessarily departing from the scope of this disclosure.

In addition, the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An articulating surgical rod bender assembly, comprising:
   a first support member;
   a second support member attached to the first support member such that the second support member is moveable relative to the first support member, the second support member comprising a plurality of arms that are connected together, at least two of the plurality of arms being pivotably connected to the first support member at spaced apart locations and at least two of the plurality of arms being pivotably connected together, the plurality of arms including an elongated first arm pivotably connected to the first support member and which can be manually pivoted between a first position and a second position;
   a first drive wheel rotatably attached to the first support member;
   means for rotating the first drive wheel;
   a second drive wheel rotatably attached to the first support member, the second drive wheel being coupled with the first drive wheel so that rotation of the first drive wheel causes rotation of the second drive wheel; and
   a guide element attached to the second support member such that movement of the second support member relative to the first support member causes movement of the guide element relative to one or more of the first drive wheel and the second drive wheel, wherein pivoting the first arm between the first position and the second position moves the guide element under a mechanical advantage,
   the first drive wheel, second drive wheel, and guide element being selectively positionable into a plurality of clamping positions, each clamping position being configured so that a surgical rod can be positioned with a first side of the surgical rod contacting the first drive wheel, an opposing second side of the surgical rod contacting the second drive wheel, and one of the first side of the surgical rod and the second side of the surgical rod contacting the guide element.

2. The rod bender assembly of claim 1, wherein the means for rotating the first drive wheel comprises a gear assembly, the gear assembly comprising:
   a first gearing member connect to the first drive wheel; and
   a second gearing member connected to the second drive wheel and to the first gearing member such that rotation of the first drive wheel rotates the first gearing member, rotation of the first gearing member rotates the second gearing member, and rotation of the second gearing member rotates the second drive wheel.

3. The rod bender assembly of claim 2, wherein the gear assembly further comprises at least a third gearing member connected to the first gearing member and second gearing member such that a mechanical advantage is achieved in rotating the second drive wheel via rotating the first drive wheel.

4. The rod bender assembly of claim 2, wherein the first drive wheel and second drive wheel are disposed on a first side of the first support member and the gear assembly is disposed on a second side of the first support member opposite the first side of the first support member, the gear assembly further comprising a first axle element connecting the first drive wheel to the first gearing member and a second axle element connecting the second drive wheel to the second gearing member, wherein the first and second axle elements are centrally supported by the first support member.

5. The rod bender assembly of claim 2, wherein the first support member comprises a frame in the form of a panel having a front face and an opposing back face, the first gearing member and the second gearing member being disposed adjacent to the front face of the frame and the first drive wheel and second drive wheel being disposed adjacent to the back face of the frame.

6. The rod bender assembly of claim 5, further comprising a mounting flange orthogonally projecting from the front face or the back face of the frame.

7. The rod bender assembly of claim 1, wherein the guide element is rotatably attached to the second support member.

8. The rod bender assembly of claim 1, further comprising a securing mechanism configured to retain the first support member in the plurality of clamping positions relative to the second support member.

9. The rod bender assembly of claim 1, further comprising a rod cutting assembly comprising a first rod cutting element connected to the first support member and a second rod cutting element connected to the second support member, the first and second rod cutting elements each having a receiving opening extending therethrough, the second rod cutting element being moveable relative to the first rod cutting element.

10. The rod bender assembly of claim 1, wherein the first arm moves along a plane as the first arm moves between the first position and the second position.

11. The rod bender assembly of claim 1, wherein the plurality of arms further comprise a second arm connected to the first arm, a third arm connected to the second arm, and a fourth arm connected to the third arm.

12. The rod bender assembly of claim 11, wherein the guide element is rotatably connected to the fourth arm.

13. The rod bender assembly of claim 1, further comprising:
the first arm having a first end and an opposing send end, the first end being pivotably coupled to the first support member; and
a securing mechanism that selectively secures the second end of the first arm to the first support member when the first arm is in the first position and the second position.

* * * * *